United States Patent [19]

Cheng

[11] Patent Number: 4,480,038

[45] Date of Patent: Oct. 30, 1984

[54] DENSITY SEPARATION OF PROTEIN OVERPRODUCING BACTERIA

[75] Inventor: Yih-Shyun E. Cheng, Wilmington, Del.

[73] Assignee: E. I. DuPont de Nemours and Company, Wilmington, Del.

[21] Appl. No.: 373,702

[22] Filed: Apr. 30, 1982

[51] Int. Cl.$^3$ .......................... C12N 1/00; C12N 1/20; C12N 1/02; C12N 15/00; C12Q 1/29; C12Q 1/04; C12P 21/00; C12P 21/02

[52] U.S. Cl. ...................................... 435/261; 435/243; 435/261; 435/29; 435/34; 435/68; 435/70; 435/172.3; 935/60; 935/72; 935/73; 935/111; 935/13; 935/14

[58] Field of Search .................. 435/29, 34, 253, 243, 435/68, 70, 172, 261

[56] References Cited

U.S. PATENT DOCUMENTS 3,072,538 1/1963 Baptist ................................. 195/101
4,138,291 2/1979 Lafferty ................................ 195/47

OTHER PUBLICATIONS

Lehninger: *Biochemistry*, Worth Publishers, Inc., New York, 1970, p. 20.
Goeddel et al., Proc. Natl. Acad. Sci. 76, pp. 106 to 110, (1979).
Cheng et al., Gene 14, pp. 121 to 130, (1981).
Novick et al., Cell., 21, pp. 205 to 215 (1980).
Nishizawa et al., Abstract of the 1981 Meeting of the *Molecular Biology of Yeast*, Cold Spring Harbor Laboratory, Cold Spring Harbor, N.Y.
Williams et al., Science 215, pp. 687 to 689, (1982).

*Primary Examiner*—Thomas Wiseman
*Assistant Examiner*—James Martinell
*Attorney, Agent, or Firm*—James A. Costello

[57] ABSTRACT

Bacterial compositions and a method for separating protein overproducing bacteria from bacteria which do not overproduce protein. The separation makes use of an increase in density of the protein overproducing bacteria relative to that of normal bacteria.

5 Claims, No Drawings

DENSITY SEPARATION OF PROTEIN OVERPRODUCING BACTERIA

BACKGROUND OF THE INVENTION

1. Field Of The Invention

Protein overproducing bacterial cells are separated from less dense bacterial cells which do not overproduce protein.

2. State Of The Art

It is known to employ gene splicing technology to overproduce proteins in microorganisms into which genes are spliced that code for said proteins. For the optimal synthesis of proteins encoded by the spliced genes, it is necessary to join several deoxyribonucleic acid (DNA) pieces in a very precise manner. Since the construction of spliced DNA molecules requires multiple steps of enzymatic reactions, the chance of successful construction may be quite low. As a result, screening a large number of bacterial clones is often necessary to isolate those having the desired recombinant DNA structures. The process of this invention allows rapid segregation of bacteria having the desired construction from those which do not.

Protein production in gram-negative, enterobacteria such as *E. coli* using recombinant DNA technology has been demonstrated by a number of investigators. For instance, Goeddel et al., Proc. Natl. Acad. Sci. 76, pages 106 to 110 (1979), describe the use of *E. coli* cells carrying recombinant plasmid pIB1 in the synthesis of a hybrid insulin A chain-$\beta$-galactosidase protein in up to 20% of the total cell protein. Cheng et al., Gene 14, pages 121 to 130 (1981), describe the bacterial synthesis of $\beta$-galactosidase in up to 15% of the total *E. coli* protein. In both cases, the proteins synthesized form intracellular protein aggregates.

U.S. Pat. No. 3,072,538, discloses a method of separating strains of living soil bacteria capable of synthesizing poly ($\beta$-hydroxybutyric acid) from other strains by density separation in an aqueous suspension. The bacteria capable of producing the polyester sink into the suspension. U.S. Pat. No. 4,138,291, discloses a method of obtaining selected bacterial strains capable of converting a carbon source into poly(D-3-hydroxybutyric acid). The selection process depends on specific weight differences. The following publications disclose the use of density gradient separation of temperature-sensitive mutants of the yeast *Saccharomyces cerevisiae:* Novick et al., Cell., 21, page 205 to 215 (1980); and Nishizawa et al., Abstract of the 1981 Meeting of the *Molecular Biology of Yeast*, Cold Spring Harbor Laboratory, Cold Spring Harbor, N.Y.

Nowhere in the literature, however, has any report been found concerning the unusual physiological property of a density increase in protein overproducing cells versus like cells which do not overproduce proteins. The discovery of this characteristic density difference allows rapid detection, identification, isolation, enrichment and recovery of protein overproducing bacteria from admixture with bacterial clones that do not have such property.

SUMMARY OF THE INVENTION

This invention comprises a method for separating gram-negative, protein overproducing bacteria from admixture with like bacteria which do not overproduce protein. The method comprises fractionating the admixture, based on density difference between said bacteria, into (i) a fraction richer in protein overproducing bacteria than in normal bacteria and (ii) a fraction richer in normal bacteria than in protein overproducing bacteria, fraction (i) being at least about 0.02 g/ml more dense than fraction (ii) after growth stops. Fraction (i) can be isolated from fraction (ii) by routine physical separation means.

The term "protein overproducing bacteria" is employed herein to designate bacteria successfully modified by recombinant DNA technology to produce proteins of the type and quantity not otherwise possible for that bacteria. The particular technique by which the bacteria are modified is not a factor in the successful operation of this invention which concerns density fractionation of protein overproducing bacteria from normal bacteria that do not overproduce protein, regardless of the manner or technique by which said bacteria were modified.

One skilled in the art with the present disclosure before him will appreciate that this invention has broad implications. For example, a mixture of bacteria of two or more distinct taxonomies, one or more of which taxonomic strains have been modified to overproduce proteins, can be fractionated according to the process of this invention to form several distinct fractions, each fraction characterized by having a greater density than the fraction above it. Detection, identification, isolation, enrichment and recovery of any particular fraction(s) can be accomplished by techniques well known in the art.

A simple embodiment of this invention is as an analytical tool to determine whether and to what extent recombinant DNA techniques have successfully modified bacteria to overproduce protein. In such an embodiment, the degree of modification can be estimated by the relative amounts of bacteria in each of the two (or more) fractions which are formed after density fractionation.

In regard to the manner of separation, several techniques are known which utilize density difference to separate cells having different densities. Such techniques include zone centrifugation, sedimentation field flow fractionation, alternative continuous flow centrifugation, and equilibrium density gradient centrifugation. It is preferred in the process of this invention to employ equilibrium density gradient centrifugation in a suitable medium such as colloidal silica particles coated with poly(vinylpyrrolidone) [percoll], sucrose, glycerol, cesium chloride, and the like. Percoll is the preferred medium.

The density separation process of this invention can be employed with bacteria which are also encoded to produce some other useful biological agent or activity, regardless whether said other biological agent or activity appears in the more dense or less dense cell fraction, provided the density differences described herein are not compromised by said other agent or activity.

This invention also concerns a bacterial composition comprising at least one bacterial strain from the group Salmonella, Shigella and Escherichia, said composition characterized by the presence therein of at least two fractions comprising (i) a fraction richer in protein overproducing bacteria than in normal bacteria and (ii) a fraction richer in normal bacteria than in protein overproducing bacteria, fraction (i) being at least about 0.02 g/ml more dense than fraction (ii).

This invention also concerns a bacterial composition comprising at least one bacterial strain from the group Salmonella, Shigella and Escherichia, said composition characterized by being richer in protein overproducing bacteria than in normal bacteria of the same strain to the extent that the density of said composition is at least about 0.02 g/ml greater than the density of the normal bacteria. This bacterial composition comprises the fraction enriched in protein overproducing bacteria separated from the fraction enriched in normal bacteria.

DETAILS OF THE INVENTION

The range of bacteria and the range of proteins whose overproduction causes the characteristic increase in density vary widely and all are contemplated to be processable according to this invention. For instance, differences of as little as 0.02 or 0.03 g/ml are sufficient to permit utilization of the process of this invention. It is preferred that there be a density difference of 0.03 g/ml or greater for best results.

Preferred bacteria include those which do not secrete protein, including enterobacteria such as bacterial strains in the genera of Salmonella, Shigella, and Escherichia. Of these genera, *Escherichia coli (E. coli)* is the most preferred strain.

After growth stops, normal *E. coli* bacterial cells have been found to have a density of about 1.08 to 1.09 g/ml and protein overproducing *E. coli* cells have a density of about 1.11 to 1.13 g/ml. As noted above, regardless of the bacterial strain or genes contained therein, or of the density of normal cells or protein overproducing cells, such overproducing cells can be detected and isolated from admixture with normal cells when the density difference is about 0.02 g/ml or more.

The type of protein being overproduced can also vary according to the coding DNA inserted into the host bacteria. Samples of representative proteins include chimeric $\beta$-galactosidase-proinsulin, human growth hormone, human $\alpha$-interferon, $\beta$-galactosidase, and X-90 which is similar to $\beta$-galactosidase but lacking 17 amino acids. Other proteins whose overproduction will lead to increased bacteria density will be obvious to those skilled in the art from a study of this disclosure as will be the manner of separating bacteria which have overproduced said protein(s) from normal bacteria which have not.

Protein overproducing bacteria are useful for making proteins which, in their own right, have various diagnostic, analytical and pharmacological utilities. For example, $\beta$-galactosidase is useful because of its enzymatic activity to cleave $\beta$-galactosyl bonds. It can be used to convert the lactose in milk whey to glucose and galactose. It can also be employed to alter blood cell surface sugar structures.

Several methods can be employed to collect cells from different density regions of an equilibrium density gradient centrifugation medium. It is possible, for example, to punch a small hole at the bottom of the centrifuge tubes and to collect the fractions with the desired densities. Alternatively, a needle attached to a syringe can be used to pierce the wall of the tubes and withdraw the desired amount of cell suspension of particular buoyant density. The collected bacterial suspensions can be diluted with isotonic buffer and centrifuged at low speed to remove the percoll. The cell pellets can then be resuspended for further analysis or growth.

The following Examples illustrate preferred embodiments of this invention. All parts and percentages are by weight, and all degrees are Celsius unless otherwise noted. This general procedure was employed: *E. coli* cells were grown at 30° to 37° in nutrient broth, e.g., Luria's broth, supplemented with 20 $\mu$g/ml of tetracycline, and the cells were harvested at 30 to 50 hr after the end of exponential growth. The harvested cell cultures were chilled with ice for 10 min, then the cells were pelleted by low speed centrifugation.

The cell pellets were washed using sterile phosphate-buffered saline or other isotonic buffers, and they were pelleted again by centrifugation. The washed cells were resuspended in sterile 60% percoll (Pharmacia) which contained 25 mM sucrose and a small amount of density marker mixture (Pharmacia). The cell suspensions were then transferred into sterile centrifuge tubes and centrifuged in a fixed angle rotor at 10° with a centrifugal force of 100,000$\times$g for 45 min. At the end of the centrifugation, the centrifuge tubes were carefully removed. Under these centrifugation conditions, the density markers formed distinct bands indicating the density gradient generated by centrifugation.

For the analysis of protein production, the *E. coli* cell pellets, after being harvested by centrifugation, were lyzed by heating at 100° for 2 min in 1% sodium dodecyl sulfate (SDS), and the proteins in cell lysates were separated by sodium dodecyl sulfate-polyacrylamide gel electrophoresis (SDS-PAGE) as described by Laemmli, Nature, 227, page 680 to 685 (1970). After electrophoresis, the separated protein bands in SDS polyacrylamide gels were detected by staining using Coomassie brilliant blue.

The procedures used to count cells and to determine the bacterial lac gene function are described by Miller, in "Experiments in Molecular Genetics", pages 31 to 36 and pages 53 to 55, Cold Spring Harbor Laboratory, Cold Spring Harbor, NY, 1972. The methods used for the isolation of plasmid DNA and the transformation of *E. coli* cells are described by Davis et al., in "Advanced Bacterial Genetics", pages 116 to 125 and pages 140 to 141, Cold Spring Harbor Laboratory, Cold Spring Harbor, NY, 1980.

For the isolation of spontaneous mutants or revertants, $10^2$ to $10^5$ cells were plated on 5-bromo-4-chloro-3-indolyl-$\beta$-D-galactoside (Xgal) indicator plates, and bacterial clones with desired Lac properties picked and further purified by restreaking.

Deposits of the bacteria referred to in the following Examples have been made with the American Type Culture Collection (ATCC) at 12301 Parklawn Drive, Rockville, MD 20852. Accession numbers are as follows for each bacterial strain:

3341[p41-14D13]ATCC 39110
CSH50R ATCC 39111
3341[pOP203(UV-5)-3]ATCC 39112
3341R[pOP203(UV-5)-3]ATCC 39113
3341[p41-14D2]ATCC 39114.

EXAMPLE 1

For comparison of the cell buoyant densities of normal and protein overproducing *E. coli* cells, two strains were chosen. The strain 3341 [p41-14D13] was a stable derivative of 3341 [p41] (Cheng et al., Gene, 14, pages 121 to 130 (1981)). The strain, 3341R [pOP203(UV-5)-3] was derived by the introduction of the plasmid [pOP20-3(UV-5)-3] (Kwoh et al., Virology, 101, pages 419 to 431, (1980)) into the strain 3341R which is a Lac+ derivative of 3341 isolated as a blue colony on Xgal indicator plates. These two strains have identical chromosomal genes except that for the lac gene. The strain 3341 [p41-14D13] is Lac−, but the strain 3341R [pOP203(UV-5)-3] is Lac+. The difference in the lac gene of these two strains was used for scoring the number of bacteria of either strain from a mixture of the two. The primary difference between these two strains, however, is their plasmid structures; the plasmid p41-14D13 encoded the synthesis in *E. coli* of an inactive β-galactosidase, X-90 protein, while the plasmid pOP203(UV-5)-3 did not encode the synthesis of any protein at elevated levels.

These two strains were grown in Luria's broth supplemented with 20 μg/ml of tetracycline, and the cells were harvested at 50 hr after the end of exponential growth. The cells were chilled in ice and were spun down, and the cell pellets were washed with isotonic buffer and were centrifuged in 60% percoll as described in the general procedure. The bacteria of 3341R [pOP203(UV-5)-3] were found to be concentrated in a region with a buoyant density of 1.090 g/ml, while the cells of the protein overproducing *E. coli*, 3341 [p41-14D13] were mainly distributed in the percoll gradient with a buoyant density of greater than 1.120 g/ml. In addition, these two strains of cells were mixed, and the mixture was centrifuged in 60% percoll as usual. At the end of the centrifugation, cells were found to be concentrated at both density regions as expected. This result demonstrated that the protein overproducing *E. coli* cells have higher than normal buoyant densities, and that they can be physically separated from the normal cells of lower buoyant density.

To further confirm the physical separation and enrichment of the protein overproducing *E. coli* cells, aliquots from different regions of the percoll gradient with different buoyant densities were collected. The cell number of 3341R [pOP203(UV-5)-3] and that of 3341 [p41-14D13] were counted before and after the percoll density gradient centrifugation, and the ratio of the two compared. A mixture of 3341R [pOP203(UV-5)-3] and 3341 [p41-14D13], with a ratio of 9:1 before centrifugation, was used for this analysis. After the percoll centrifugation, the cell suspension isolated from a gradient region with a buoyant density of 1.120 g/ml was found to have a 3341 [p41-14D13] to 3341R [pOP203(UV-5)-3] ratio of 4:1. The nearly 40-fold enrichment of protein overproducing cells was achieved by a single step of gradient centrifugation.

EXAMPLE 2

In this Example, a series of experiments compare the properties of normal and protein overproducing *E. coli* strains. The strain 3341 [pOP203(UV-5)-3], a Lac− 3341 transformant by plasmid pOP203(UV-5)-3, produced normal levels of cellular proteins. The strain 3341 [p41-14D2] was a Lac+ derivative of 3341 [p41] due to the spontaneous reversion of the lac Z-X90 to a wild type form. This strain produces the protein β-galactosidase in up to 15% of the total cell protein. The strain 3341 [p41-14D13], described in Example 1, was also used.

*E. coli* cells were grown in Luria's broth supplemented with 20 μg/ml of tetracycline at 37°, and the cells were harvested at 40 hr after the end of exponential growth. The harvested cells were centrifuged in 60% percoll under the conditions described in the general procedure. The protein overproducing *E. coli* cells were found to have an average buoyant density of 1.110 to 1.120 g/ml, whereas the normal *E. coli*, 3341 [pOP203(UV-5)-3], had a buoyant density of 1.090 g/ml. Several percoll density gradient centrifugations were run using mixtures of 3341 [p41-14D2] and 3341 [pOP203(UV-5)-3] cells or mixtures of 3341 [p41-14D13] and 3341 [pOP203 (UV-5)-3] cells. After the percoll gradient centrifugation, cell suspensions were isolated from different density regions ranging from 1.110 g/ml to 1.130 g/ml. An 8 to 40 fold enrichment of the protein overproducing cells was found among these isolated cell suspensions. The greatest enrichment was achieved in cell suspensions collected from a density region of 1.122 g/ml.

EXAMPLE 3

This Example demonstrates that *E. coli* K12 cells in general can be used for the identification and enrichment of protein overproducing derivatives. A plasmid DNA mixture containing pOP203(UV-5)-3, p41-14D13, and p41-14D2 was used to transform the *E. coli* strain, CSH50R, which was a derivative of CSH50 (Cheng et al., Gene, 14, pages 121 to 130 (1981)) carrying a rec A mutation constructed by conjugation. Transformants of CSH50R were isolated by their resistance to tetracycline. Among these transformants, 38 strains were randomly picked for buoyant density analysis. These cells were grown up in Luria's broth supplemented with 20 μg/ml of tetracycline and harvested at 50 hr after the end of their exponential growth. The harvested cells were washed with isotonic buffer and were centrifuged in 60% percoll as described in the general procedure.

Thirty-three of the 38 isolates tested had a buoyant density of greater than 1.116 g/ml. These cells were further tested for their protein production. The results showed that all high density isolates produced either β-galatosidase or X-90 proteins at a level greater than 10% of the total cellular protein. The remaining five isolates were found to have insignificant or undetectable cell populations with a buoyant density of greater than 1.116 g/ml. Furthermore, protein analysis of these isolates indicated that neither β-galactosidase nor X-90 protein was produced by any one of these five isolates. The results are summarized in Table 1.

TABLE 1

| PROPERTIES OF CSH50R[a] TRANSFORMANTS | | | |
|---|---|---|---|
| Isolate | Lac[b] | Protein Over-production[c] | Buoyant Density[d] (g/ml) |
| 1 | − | − | 1.082 |
| 2 | − | X-90 | 1.120 |
| 3 | − | X-90 | 1.121 |
| 4 | − | X-90 | 1.122 |
| 5 | + | β-galactosidase | 1.118 |
| 6 | − | X-90 | 1.119 |
| 7 | − | X-90 | 1.120 |
| 8 | − | − | 1.083 |
| 9 | + | β-galactosidase | 1.122 |
| 10 | − | X-90 | 1.122 |
| 11 | − | X-90 | 1.122 |
| 12 | − | X-90 | 1.120 |
| 13 | − | X-90 | 1.121 |
| 14 | − | X-90 | 1.119 |
| 15 | − | − | 1.085 |
| 16 | − | X-90 | 1.119 |
| 17 | − | X-90 | 1.120 |
| 18 | − | X-90 | 1.117 |
| 19 | − | X-90 | 1.119 |
| 20 | − | X-90 | 1.121 |
| 21 | − | X-90 | 1.120 |
| 22 | − | X-90 | 1.119 |
| 23 | − | X-90 | 1.120 |
| 24 | − | X-90 | 1.117 |
| 25 | − | X-90 | 1.116 |
| 26 | − | X-90 | 1.121 |
| 27 | + | β-galactosidase | 1.122 |

TABLE 1-continued

PROPERTIES OF CSH50R[a] TRANSFORMANTS

| Isolate | Lac[b] | Protein Over-production[c] | Buoyant Density[d] (g/ml) |
|---|---|---|---|
| 28 | − | X-90 | 1.122 |
| 29 | − | X-90 | 1.120 |
| 30 | − | X-90 | 1.119 |
| 31 | − | X-90 | 1.120 |
| 32 | − | X-90 | 1.119 |
| 33 | + | β-galacotisdase | 1.115 |
| 34 | − | — | 1.089 |
| 35 | − | X-90 | 1.119 |
| 36 | − | X-90 | 1.120 |
| 37 | − | X-90 | 1.120 |
| 38 | − | — | 1.088 |

[a] A bacterial strain of the following description: F−, ara, Δ(pro,lac), thi, rpsL, rec A.
[b] Ability to use lactose.
[c] Any protein produced at a level equal or higher than 10% of total cell protein, e.g., high level protein production.
[d] Measured by percoll density gradient centrifugation.

The embodiments of the invention in which an exclusive property or privilege is claimed are defined as follows:

1. A method for separating protein overproducing $E.$ $coli$ bacteria from admixture with normal $E.$ $coli$ bacteria that do not overproduce protein the separation method being applied after bacterial growth stops, comprising fractionating the admixture, based on density difference between said bacteria, into (i) a fraction richer in protein overproducing bacteria than in normal bacteria and (ii) a fraction richer in normal bacteria than in protein overproducing bacteria, fraction (i) being at least about 0.02 g/ml more dense than fraction (ii) after growth stops.

2. A method according to claim 1 comprising the additional step of isolating fraction (i) from fraction (ii).

3. A method according to claim 1 or claim 2 wherein the protein is selected from the group consisting essentially of β-galactosidase, X-90, human growth hormone, human α-interferon, and chimeric β-galactosidase-proinsulin.

4. A method according to claim 3 wherein the protein is β-galactosidase.

5. A method according to claim 3 wherein the protein is X-90.

* * * * *